United States Patent
Bringley

(10) Patent No.: US 12,178,673 B2
(45) Date of Patent: Dec. 31, 2024

(54) SHADE MATCHING DENTAL COMPOSITE

(71) Applicant: Joseph F. Bringley, Rochester, NY (US)

(72) Inventor: Joseph F. Bringley, Rochester, NY (US)

( * ) Notice: Subject to any disclaimer, the term of this patent is extended or adjusted under 35 U.S.C. 154(b) by 740 days.

(21) Appl. No.: 17/004,977

(22) Filed: Aug. 27, 2020

(65) Prior Publication Data

US 2021/0059798 A1 Mar. 4, 2021

Related U.S. Application Data

(60) Provisional application No. 62/893,491, filed on Aug. 29, 2019.

(51) Int. Cl.
| | |
|---|---|
| *A61C 13/08* | (2006.01) |
| *A61K 6/16* | (2020.01) |
| *A61K 6/17* | (2020.01) |
| *A61K 6/62* | (2020.01) |
| *A61K 6/71* | (2020.01) |
| *A61K 6/80* | (2020.01) |

(52) U.S. Cl.
CPC .............. *A61C 13/082* (2013.01); *A61K 6/16* (2020.01); *A61K 6/17* (2020.01); *A61K 6/62* (2020.01); *A61K 6/71* (2020.01); *A61K 6/80* (2020.01)

(58) Field of Classification Search
CPC .................................................. A61C 13/082
See application file for complete search history.

(56) References Cited

U.S. PATENT DOCUMENTS

| | | | |
|---|---|---|---|
| 9,132,068 B2 | 9/2015 | Toriyabe et al. | |
| 10,828,240 B2 * | 11/2020 | Fukudome | A61K 6/76 |
| 11,078,303 B2 * | 8/2021 | Akizumi | A61K 6/887 |
| 11,273,018 B2 * | 3/2022 | Böhm | A61C 13/083 |
| 2003/0069325 A1 * | 4/2003 | Konings | A61K 6/884 |
| | | | 523/105 |
| 2017/0143594 A1 * | 5/2017 | Lu | A61K 6/69 |
| 2018/0303721 A1 | 10/2018 | Akizumi et al. | |

FOREIGN PATENT DOCUMENTS

| | | | | |
|---|---|---|---|---|
| CA | 2898793 A1 * | 8/2014 | ......... | A61C 13/0004 |
| WO | WO-2015034881 A1 * | 3/2015 | ............... | A61K 6/02 |
| WO | WO-2018042001 A1 * | 3/2018 | ......... | A61C 13/0022 |
| WO | WO-2018043595 A1 * | 3/2018 | ........... | A61K 6/0073 |
| WO | WO-2018101236 A1 * | 6/2018 | ............... | A61K 6/08 |

OTHER PUBLICATIONS

Pfaff, Becker "Special effect pigments in cosmetic applications An amazing development for a bright future" Series: Colour Cosmetics Househld & Personal Care today—n Jan. 2012.

Carmi Weingrod "Three-Dimensional Color and Interference Pigments" Daniel Smith, 2020, http://danielsmith.com/blogs/three-dimensional-color-and-interference-pigments/.

* cited by examiner

*Primary Examiner* — Michael F Pepitone
(74) *Attorney, Agent, or Firm* — Lynne M. Blank, Esq.

(57) ABSTRACT

A dental composite or coating that comprises at least one photopolymerizable resin, at least one inorganic filler, a photoinitator, and at lease one interference platelet. The dental composite is able to adapt and match the color and shade of adjacent tooth structure in the cavity in which it is placed, without the need for conventional dyes and pigments, although it may be desirable to use dyes and pigments in a specific shade series.

20 Claims, No Drawings

SHADE MATCHING DENTAL COMPOSITE

CROSS REFERENCE TO RELATED APPLICATIONS

Priority is claimed and reference is made to commonly assigned, U.S. Prov. Patent Application No. 62/893,491 by Bringley et al., filed Aug. 29, 2019 entitled "SHADE MATCHING DENTAL COMPOSITE", the disclosure of which is incorporated herein by reference.

FIELD OF THE INVENTION

The present invention relates to photopolymerizable composites and coatings, and particularly to dental composites. The composite or coating comprises at least one photopolymerizable resin, at least one inorganic filler, a photoinitator, and an interference platelet. The dental composite is able to adapt, and to match the color and shade of adjacent tooth structure in the cavity in which it is placed. The invention relates to any dental photopolymerizable composite or dental restoration within the oral cavity.

BACKGROUND OF THE INVENTION

Inorganic-organic polymer composite materials are used in a wide variety of applications including structural materials, high performance composites, optical components, aerospace, biomedical implants, and dental applications. Generally, composites are employed where performance requirements are demanding and not easily fulfilled with traditional structural materials. For example, inorganic materials such as glass, ceramic and stone are very hard, scratch resistant and even sometimes transparent (e.g., glass) but suffer from the fact that they are very heavy and brittle. Polymers, conversely, are light and durable but have poor hardness, abrasion, and wear resistance. Composites, made from the combination of inorganic materials and polymers, may have properties that lie in between, potentially providing materials that are strong but lightweight, hard but flexible, abrasion resistant and durable.

The dental industry, primarily due to health concerns, is rapidly transitioning dental restoratives (e.g., cavity fillings, dental restorations, adhesives, etc.) from the conventional mercury-based amalgams to highly filled, light curable, resin based composites. Resin based composites are safer and better match the color and appearance of human tooth enamel, but are often softer, not as strong, or as durable as the traditional metal amalgams. To resolve these problems, manufacturers have developed micro- and nano-filled polymer composites that have strength, hardness, and durability close to that of the conventional amalgams. Typically, the resin based composite paste is applied or packed into a tooth cavity and then cured using a hand-held light wand. The wand is held in proximity of the composite for a period of time necessary to fully cure the paste with the intention to create a hard, strong, and durable composite, that closely matches appearance and function of natural tooth structure.

The aesthetic appearance of the restoration is paramount. Ideally, the restoration should match the patient's healthy teeth in color and lightness as closely as possible. Since human teeth vary in color and lightness from person to person, the dental restorations contain dyes and/or pigments that are placed within the restorative to provide various shades, which can then be chosen by the dentist so that the restoration will not have a color and lightness that is perceptibly different than the patients healthy teeth, especially those adjacent to the restoration. In addition, human teeth are translucent in appearance giving them optical brilliance, and this further increases the challenge of matching the aesthetic character of adjacent teeth.

There are a variety of shade guides for a dental practitioner to match the color of human teeth. The classical shade guide was introduced by VITA in 1956 (Vita North America, Yorba Linda, CA, USA). In the classical shade guide, the shades that represent the color variation across the human population are the "A" shades (A1-A4), the "B" shades (B1-B4), the "C" shades (C1-C4) and the "D" shades (D1-D4); wherein the A-shades have a reddish-brownish appearance, the B-shades are reddish-yellowish, the C-shades are grayish and the D-shades are reddish-grey. In addition, there are other commercial shade guides, some of which contain as many as 32 distinct shades. Known examples are Chromoscop® (Ivoclar Vivadent) and Esthet-X (Dentsply, Inc.). Technical details and a review of the various shade guides is given in "A Review of Color Science in Dentistry: Shade Matching in the Contemporary Dental Practice" J. C. Ragain, in *J. Dentistry, Oral Disorders & Therap.* (2016).

There is a significant clinical problem in that a dentist must carry as many as sixteen different shades in order to correctly match the tooth shade of a given patient. This is greatly inefficient for the dentist since she or he is forced to carry a significant inventory of colors, and moreover because shades are often wasted due to the expiration of the product. This is further inconvenient and challenging for dental manufacturers since they are forced to manufacture and inventory sixteen, and sometimes as many as 32, shades across numerous dental tooth restorative products. It would be beneficial if a restoration could adapt to the color of adjacent tooth structure and decrease the number of shade matching colors that a dentist may carry.

United States Patent Application 2018/0303721A1 to Akizumi et al., discloses a curable composition which is useful for application as a dental composite. The invention relates to a curable composition that can have the external appearance and color tone well-controlled without using a dye or a pigment. The curable composition is obtained by selecting a spherical filler having a particle size between 230 and 1000 nm and having a very narrow particle size distribution. The curable composition "enables restoration by which the external appearance of the cured article formed therefrom matches the appearance of natural teeth". There is a problem, however, in that the filler particles having a specific size and narrow distribution are exceedingly difficult to prepare. There is an additional problem in that the color tone adaptability of the composition is inadequate and poorly defined.

Problem to be Solved

The inventors have recognized a problem in that there is, currently, a lack of useful methods of achieving color adaptability in a dental composite and that multiple dental shades are still necessary. There is a need for a curable composition that can adapt to the background color of the cavity in which it is placed. There is a need for a "universal" dental composite that could replace the sixteen shades used in dentistry with a single adaptable shade. There is a need for dental composites that could reduce the number of shades necessary, say for example from sixteen to four: one composite for all the A-shades, one for the B-shades, one for the C-shades and one for the D-shades.

SUMMARY OF THE INVENTION

The invention provides a dental composite or coating that comprises at least one photopolymerizable resin, at least one inorganic filler, a photoinitator, and at least one interference platelet. The dental composite is able to adapt and match the color and shade of adjacent tooth structure in the cavity in which it is placed, without the need for conventional dyes and pigments, although it may be desirable to use dyes and pigments in a specific shade series.

Advantageous Effect of the Invention

The invention provides a curable composition that can adapt in color to the adjacent tooth structure and eliminates or reduces the need for multiple shades.

DETAILED DESCRIPTION OF THE INVENTION

The invention is directed toward photopolymerizable composites and coatings, and especially to dental composites. The invention discloses a curable dental composition comprising a photocurable resin, at least one filler, a photoinitiator and at least one interference platelet. In one preferred embodiment, the contrast ratio of a disk of 1 mm thickness of the cured composite is between 40 and 85. The dental composite, when cured, is able to adapt and match the shade of adjacent tooth structure in the cavity in which it is placed. The invention relates to any dental composite and/or coatings.

Terms and Definitions

A photopolymer is any monomer, group of monomers, oligomer, pre-polymer, or polymer capable of being polymerized or cured by electromagnetic radiation having a wavelength of less than about 2000 microns.

"Polymerized" and "cured" are used herein interchangeably and mean the same; photopolymerized and photocured also mean the same.

Photopolymerization or photopolymerizable, photocurable and light curable as used herein, refers to a process, or materials, in which monomers, oligomers or pre-polymers (hereafter collectively referred to as resins) are polymerized or cured using electromagnetic radiation, such as X-rays, electron beams, and ultraviolet and actinic light.

An interference platelet as used herein refers to a colorless microparticle whose thickness is selected such that it reflects or scatters specific colors or wavelengths of light.

The term translucent, as used herein, means that an object may permit the passage of light, especially actinic light. A translucent object is transmitting to light in a manner such that objects in the background are discerned but cannot be observed clearly. Another term, roughly equivalent to translucent, is semi-transparent.

The invention provides a curable composition that can adapt in color to the adjacent tooth structure and eliminates the need for multiple shades. The invention discloses a curable dental composition comprising a photocurable resin, at least one filler, a photoinitiator and at least one interference platelet.

Color adaptation and structural color is an emerging field in science and engineering. Structural color is essentially color that is created by the physical structure of a material, as opposed to color that is created by chemical dyes and pigments. Structural color is abundant in nature as it is found in gemstones such as opal, in the colors of butterflies and chameleons where periodic nanostructures display remarkable color due to their interaction with light waves. The authors of the current invention have found, surprisingly, that color adaptability can be achieved by reflecting or bouncing the incoming (actinic) light off the "cavity walls" that surround the dental restoration. The term "cavity walls" specifically refers to the natural tooth structure (both the walls and the floor) in which the restoration is placed. As the light is reflected off the surfaces that comprise the cavity, the light mimics the color of the cavity and can be shown to adapt to the color of the adjacent tooth structure.

The invention discloses a curable dental composition comprising a light curable resin. The light curable resin may be selected from any photopolymerizable molecule, monomer, oligomer, or prepolymer (hereafter light curable resins). Particularly preferred light curable resins suitable for use in the application of the invention include hardenable organic materials having sufficient strength, hydrolytic stability, and nontoxicity to render them suitable for use in the oral or in vivo environment. Examples of such materials include acrylates, methacrylates, urethanes, carbamoylisocyanurates, epoxides, and mixtures and derivatives thereof. One class of preferred hardenable materials includes materials having polymerizable components with free radically active functional groups. Examples of such materials include monomers having one or more ethylenically unsaturated group, oligomers having one or more ethylenically unsaturated group, polymers having one or more ethylenically unsaturated group, and combinations thereof. In the class of hardenable matrix resins having free radically active functional groups, suitable light curable components for use in the invention contain at least one ethylenically unsaturated bond and are capable of undergoing addition polymerization. Such free radically ethylenically unsaturated compounds include, for example, mono-, di- or poly-(meth)acrylates (i.e., acrylates and methacrylates), such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycoldimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)] propoxyphenyldimethylmethane, ethoxylated bisphenol A di(meth)acrylate, and trishydroxyethyl-isocyanurate trimethacrylate; (meth)acrylamides (i.e., acrylamides and methacrylamides), such as (meth)acrylamide, methylene bis-(meth)acrylamide, and diacetone (meth)acrylamide; urethane (meth)acrylates and the bis-(meth)acrylates of polyethylene glycols. Other suitable free radically polymerizable compounds include siloxane-functional (meth)acrylates and fluoropolymer functional (meth)acrylates. Mixtures of two or more free radically polymerizable compounds can be used, if desired. Other matrix materials or polymers may also be incorporated. Examples of other useful matrix polymers include natural and synthetic biopolymers, such as peptides, proteins, gelatin, poly(lactic acid), poly(glycolic acid), poly(caprolactone), chitosan and its derivatives, alginates, starches, and the like.

The dental composition of the invention typically contains a photoinitiator that is capable to absorb the incident (curing) radiation of a first wavelength and to initiate the polymerization/curing reaction. The photoinitiator may optionally be combined with a sensitizer or accelerator. The choice of photoinitiator may be dependent upon the wavelength of the curing radiation. For X-ray or electron beam radiation, a photoinitiator is not typically required since these high energy wavelengths may directly initiate polymerization. For ultraviolet curing, the photoinitiator is typically selected so that it absorbs energy between about 180-450 nm. For blue light curing, the photoinitiator is typically selected so that it absorbs energy between about 400-500 nm. Examples of suitable UV and visible photoinitiators are those sold under the trade name Irgacure® and Lucirin® (BASF Corp. Charlotte, N.C.) or under the trade name Darucor® (Ciba Specialty Chemicals). It is preferred that the photoinitiator is a blue light photoinitiator that is photobleachable. For dental or medical applications, it is preferred that the photoinitiator is camphorquinone or TPO (2,4,6-trimethylbenzoyldiphenylphosphine oxide). It is further preferred that the camphorquinone is used together with a polymerization accelerator such as an amine, or any other molecule capable of accelerating the reaction. An example of a suitable accelerator for practice of the invention is ethyl-4-N,N-dimethylamino benzoate.

The light curable coatings or composites of the invention may contain addenda such as flow agents, thickening agents, coating agents, surfactants and performance agents that improve the manufacturability of the article or improve the physical properties of the final composite or coating. In the coating industry, it is common to add performance addenda that improve adhesion, scratch resistance, hardness, and durability of the article. It is preferred that such addenda do not substantially absorb the curing radiation, since the absorbance by addenda may adversely affect the polymerization rate.

There are several methods known within the industry to counteract the absorption of curing radiation by addenda. The first is to include nanoparticles within the coating or composite formulation. Because of their small size (less than about 100 nm), nanoparticles often may not absorb or scatter the curing radiation and hence may be transparent to both the curing, emitted and visible wavelengths. A second method to control this problem is to match the refractive indices of the uncured resin and performance addenda materials. If the addenda have the same, or nearly the same, refractive index as that of the resin then the curing radiation is not significantly scattered by the performance addenda. This is especially important in the dental industry where the filler loadings are remarkably high (typically about 80 weight percent in order to obtain hardness comparable to teeth). Further, the refractive index is matched to provide a composite (tooth restoration) that is aesthetically appealing, attempting to recreate the optical translucency and visual brilliance of natural teeth.

The curable dental composition of the invention comprises at least one filler. The term "filler" is typically used to describe inorganic addenda that are placed within the composite. These inorganic materials provide strength, hardness, and durability, but also are essential to the aesthetic properties of the restoration. A wide variety of dental filler materials are available to aid formulators in achieving such properties. The filler materials, useful for the purpose of practicing the instant invention include silica-alumina, silica-titania, silica-zirconia, and silica rare-earth mixed oxides as described in H. Suzuki et al. "Refractive index adjustable fillers for visible light cured dental resin composites: preparation of $TiO_2$—$SiO_2$ glass powder by the sol gel process." *J. Dental Research.* 883 (1991) and in U.S. Pat. Nos. 4,217,264, 4,503,169, 4,764,497, 5,856,374, 6,572,693, 6,730,156, 8,617,306, 9,017,733B2, and 9,862,813 all incorporated herein by reference in their entirety. Also useful for practice of the invention are refractive index-controlled glasses, sometimes referred to as dental glasses, and exemplified most typically by barium glass or strontium glasses, available form Schott Corp. Still other useful materials are nanoparticles or nanoparticle dispersions as described in U.S. Pat. Nos. 5,609,675, 6,060,830, 6,572,693, 6,899,948 and Japanese Patent Kokai JP07-291817, all incorporated herein by reference in their entirety. Still other useful materials are fumed, colloidal or precipitated silicas, aluminas, and radiopaque materials such as zirconia, nano-zirconia, ytterbium fluoride and yttrium fluoride. It is important that the filler, or the fillers, chosen has a controllable refractive index. For purposes of achieving color adaptability, it is preferred that the refractive index difference between the cured resin and fillers is not greater than 0.06, and more preferably not greater than 0.03.

Composites may often contain more than one performance addenda (fillers), or even combinations of many fillers. In this case, the primary filler is the filler that is used in the greatest quantity. It is preferred that both the resin and the primary filler have a refractive index between about 1.44 to 1.55, and more preferably about 1.49 to 1.54. In a particularly preferred embodiment, the filler comprises at least 50% silica, wherein at least a portion of the silica has a primary particles size greater than 30 nm, and at least a portion of the silica is less than 30 nm. This is preferred because silica is a material that is easily adaptable in its refractive index, and further silica sizes can be selected such that they scatter visible light more or less strongly. Particles smaller than 30 nm scatter visible light very weakly, and tend to yield composites that are too transparent, whereas particles greater than 30 nm may scatter visible light strongly, creating composites that are too opaque. In practice of the invention it is preferred that a mixture of the primary particles is used so that the optical properties of the composite can be tuned in great detail to allow precise color adaptability.

The curable dental composition of the invention comprises at least one interference platelet. An interference platelet is a layer like structure of two or more materials which have a refractive index difference, also described as a platelet, monolith or disk-like morphology. The morphology is such that the diameter of the disk or platelet is typically about 5-100 microns, whereas the thicknesses of the disk or platelet is typically less than one micron and is chosen to form an interference pattern with actinic radiation. Such materials are also often referred to as interference colors, effect pigments or interference pigments. These materials, although themselves colorless, are able to form color through optical effects that are broadly termed structural color. The color is produced when two or more light waves interact (reflect, diffract or scatter) with the interference platelets. The interference between the waves cancels some of the frequencies that make up the white light, but not others. Constructive interference therefore results in the appearance of color in otherwise colorless materials. The interference platelets are typically made up of two or more metal-oxides such as silica, alumina, iron oxide, zinc oxide and titania. Interference platelets may also be prepared from plate-like minerals such as aluminosilicates, clays, mica, and layered oxides and hydroxides. Interference platelets may also be prepared from organic materials and plastics or, in theory, any lamellar material. Interference platelets are discussed in detail in "*Special Effect Pigments in Cosmetic Applications*", Gerard Pfaff, *Colour Cosmetics*, No. 1 (2012); and in "*Three-dimensional color and Interference Pigments*", Carmi Weingrod, http://handprint.com/HP/WCL/pigmt4.html. When selecting an interference platelet, several factors may come into play, including the dental shade to be matched, the region of the visible spectrum needed to color adapt for a given subset of dental shades, the particle size, and the specific color or colors, if multiple interference platelets are chosen. Preferably, the interference platelet is reflective or scattering in the visible region of the spectrum. Interference platelets may be selected or designed to produce virtually any spectral color. In the invention described herein it is preferred that at least one of the interference platelets produces light in the red region of the spectrum, from about 600-700 nm. Other preferred pigments are green light and yellow (or gold) producing interference platelets. These are preferred because they best match the spectral hues of natural teeth in the human population. Consequently, interference platelets having brownish and grayish tones may also be suitable for color adaptability in dental shades. In a particularly preferred embodiment, two interference platelets are employed and are selected from either red and green, or red and yellow. It is preferred that the interference platelet has a mean particle or equivalent particle diameter between 5 and 100 microns, and it is more preferred between 5 and 50 microns. This is preferred because larger platelets may produce a "grainy" color appearance. In practice of the invention it is paramount to add the desired amount of each interference platelet so that the best color match and adaptability across all dental shades can be achieved. It is preferred that the interference platelets are present in the dental composite at less than 2500 parts per million (ppm) and more preferably, interference platelets are employed at a concentration of between about 100 and 1500 ppm. In another preferred embodiment, interference platelets are selected to match as closely as possible the A shades in dentistry. This is important since the majority of patients have teeth that are best matched with A shades. It is also preferred to match C shades since this is the second most common shade of natural teeth. The curable dental composition is also preferred to match the dental D shades.

In practice of the invention it is imperative that the cured dental composite is translucent. A translucent object is transmitting to light in a manner such that objects in the background are discerned but cannot be observed clearly. If the cured dental composite is too transparent, it will appear dark in the oral cavity and will not match the color of adjacent tooth structure. If the cured dental composite is too opaque, light will not transmit within the restoration and it will appear dull with poor color adaptability to adjacent tooth structure. In dentistry, the degree of translucency is often expressed using a term called the contrast ratio. The contrast ratio (CR) is defined as the ratio of illuminance of the test material when it is placed on the black background ($L^*_b$) to the illuminance of the same material when it is placed over a white background ($L^*_w$); or $CR=(L^*_b)/(L^*_w)\times 100$. The contrast ratio is dependent upon sample thickness; but in dentistry this value is typically measured in a specimen of 1 mm thickness. The curable dental composition of the invention has a contrast ratio (for a disk of 1 mm thickness) of between 40 and 85. Dental composites having a contrast ratio below 40 are too transparent, and dental composites having a contrast above 85 are too opaque and will show poor adaptability. It is more preferred that the contrast ratio is between about 55 and 75.

The invention is directed primarily toward dental composites for use in filling cavities, and for oral reconstruction. The primary application of the invention is for restoration of anterior (front) teeth since those teeth are most visible. The invention may also be employed in dental cements, sealants, luting agents, ceramics and in any other application where adaptability to adjacent tooth structure is desired.

EXAMPLES

Materials.

All material concentrations are given as weight-to-weight percentages unless otherwise noted.

NALCO 2327® is a colloidal dispersion of silica in water, the mean silica particle diameter is 20 nm and the solids concentration 40.0%.

NALCO 1060® is a colloidal dispersion of silica in water, the mean silica particle diameter is 60 nm and the solids concentration 50.0%. Zirconyl Acetate® is a colloidal zirconia dispersion sold by Nyacol Nanotechnologies with a mean particle diameter of 5-10 nm.

Dental Resin A. The photocurable dental resin used for all experiments was a mixture of methacrylates: BisGMA, urethane dimethacrylate and triethyleneglycol dimethacrylate. The refractive index of the resin was 1.505 (before polymerization) and 1.530 (after polymerization). In all cases the resin was activated for photopolymerization using camphorquinone at 0.30 wt. % and the accelerator ethyl-4 (dimethylamino)benzoate at 0.7 wt. %.

Interference platelets were obtained from Just Pigments: satin red (CP-211), satin gold (CP-201), satin green (CP-231), pearl blue (CP-225). The satin pigments are 5-25 microns in diameter whereas the Pearl pigments are 10-60 microns in diameter.

Photocurable dental composites, Sonicfil®, A1 and A3 shades, Harmonize®, enamel and dentin shades were obtained from Kerr Dental.

Omnichroma® is a commercial dental restorative marketed by Tokuyama Dental Corp.

Methods and Testing Methods.

Photocurable dental composites were prepared by mixing fillers, resin, interference platelets, the initiator, camphorquinone and the accelerator ethy-4-(dimethylamino) benzoic acid in a Flactek, Inc. centrifugal speed mixer. The ingredients were carefully weighed into 100 cc containers and mixed for 60 seconds using a Flactek Centrifugal speedmixer operating at 2500 rpm; this operation was repeated three times to ensure complete homogeneity. The dental composite pastes were stored at 25° C. in the dark when not being used. The component compositions are given in Tables 1 and 2. The curing lamp used for all examples was a Kerr DemiUltra LED with blue light emission centered at about 470 nm and a radiant power of 1100 mW/cm². For 1 mm disk samples, CIE L*a*b* values were measured using a calibrated X-Rite® 918 tristimulus reflection colorimeter. Values were measured on standardized black and white backgrounds for calculation of the contrast ratio. The illuminance was D50 (warm daylight) at 2° incidence and 10° observation. The contrast ratio (CR) was calculated as $CR=(L^*_b)/(L^*_w)\times 100$.

For pads and cylinders (see below), CIE L*a*b* values were obtained from photographs of the examples and comparison examples taken in a light box illuminated with 5500 K daylight using the commercial program "color grab". The L*a*b* values were measured three times and averaged to ensure data quality. Color differences between the specimen ("s") (examples and comparison examples) and commercial dental shades ("c") were calculated as "delta E" where $\Delta E = SQRT[(L^*_s - L^*_c)^2 + (a^*_s - a^*_c)^2 + (b^*_s - b^*_c)^2]$. The smaller the value of delta E the better the color match. The overall color adaptability was evaluated by taking the average $\Delta E$ value for all dental shades evaluated.

Preparation of Fillers: The fillers used in all examples were heterocoagulated silica-zirconia fillers prepared according the detailed procedures in U.S. Pat. No. 8,617,306 B2 to Lambert et al., and in U.S. Pat. No. 9,017,733 B2 to Bringley et al., incorporated herein by reference. Silica/zirconia ratios were modified to tune the refractive index of the fillers. All fillers were silanated with methacryloxypropyl(trimethoxy)silane prior to use in a dental composite to facilitate homogeneous dispersion of the filler within the composite. The ratio of methacryloxypropyl(trimethoxy)silane to unsilanated powder was 0.08, weight-to-weight, in all cases.

Filler A: A heterocoagulated silica-zirconia mixed oxide with a refractive index of 1.523; the primary particle size of the silica was about 15-28 nm. The silanated filler had a mean particle diameter of 4.2 microns.

Filler B: A heterocoagulated silica-zirconia mixed oxide with a refractive index of 1.546; the primary particle size of the silica was about 55-78 nm. The silanated filler had a mean particle diameter of 3.2 microns.

Filler C: A heterocoagulated silica-zirconia mixed oxide with a refractive index of 1.518; the primary particle size of the silica was about 15-28 nm. The silanated filler had a mean particle diameter of 3.2 microns.

Filler D: A heterocoagulated silica-zirconia mixed oxide with a refractive index of 1.510; the primary particle size of the silica was about 15-28 nm. The silanated filler had a mean particle diameter of 3.4 microns.

Filler E: A heterocoagulated silica-zirconia mixed oxide with a refractive index of 1.535; the primary particle size of the silica was about 15-28 nm. The silanated filler had a mean particle diameter of 3.2 microns.

Filler F: A heterocoagulated silica-zirconia mixed oxide with a refractive index of 1.535; the silica's used had primary particle sizes 55-78 nm and 15-28 nm, respectively at a wt./wt. ratio of 2.4. The silanated filler had a mean particle diameter of 3.3 microns.

Comparison Example 1. Into a 100 cc container was carefully weighed 2.83 g of Filler A, 0.50 g of Filler B and 1.67 g of activated Dental Resin A. The contents were then mixed for 60 seconds using a Flactek centrifugal speed-mixer operating at 2500 rpm, and this operation was repeated three times to ensure complete homogeneity. Mixing was performed under vacuum to remove air bubbles or voids contained with the composite. The dental composite paste was stored at 25° C. in the dark when not being used. Cavities were filled with this dental composite, cured, and evaluated as described below.

Example 1. Example 1 was carried out in an identical manner to Comparison Example 1, except that, in addition, 0.0040 g of Satin Red CP-211 was added before mixing. The interference platelets were pre-mixed in the dental resin A in order to ensure homogeneity. The final concentration of red interference platelets was 800 ppm (or 0.08%).

Example 2. Example 2 was carried out in an identical manner to Example 1, except that the interference platelet used was satin gold CP-201 at a final concentration of 500 ppm.

Example 3. Example 3 was carried out in an identical manner to Comparison Example 1, except that the filler used was 3.25 g of Filler D, and the interference platelet used was satin red CP-211 at a final concentration of 640 ppm.

Example 4. Example 4 was carried out in an identical manner to Comparison Example 1, except that the filler used was 3.25 g of Filler C, and the interference platelet used was satin red CP-211 at a final concentration of 640 ppm.

Example 5. Example 5 was carried out in an identical manner to Comparison Example 1, except that the filler used was 3.25 g of Filler A, and the interference platelet used was satin red CP-211 at a final concentration of 640 ppm.

Comparison Example 2. Comparison Example 2 was carried out in an identical manner to Comparison Example 1, except that the filler used was 3.50 g of Filler A.

Example 6. Example 6 was carried out in an identical manner to Comparison Example 2, except that the interference platelets, satin red CP-211 and satin gold CP-201, were added at concentrations of 400 ppm each.

Example 7. Example 7 was carried out in an identical manner to Comparison Example 1, except that the filler used was 3.25 g of Filler D, and the interference platelet used was satin red CP-211 at a final concentration of 1280 ppm.

Example 8. Example 8 was carried out in an identical manner to Comparison Example 1, except that the filler used was 3.25 g of Filler C, and the interference platelet used was satin red CP-211 at a final concentration of 1280 ppm.

Example 9. Example 5 was carried out in an identical manner to Comparison Example 1, except that the filler used was 3.25 g of Filler A, and the interference platelet used was satin red CP-211 at a final concentration of 1280 ppm.

Comparison Example 3. Comparison Example 3 was carried out in an identical manner to Comparison Example 1, except that the filler used was 3.35 g of Filler D.

Example 10. Example 10 was carried out in an identical manner to Example 7, except that the interference platelets, satin red CP-211 and satin gold CP-201, were added at concentrations of 800 ppm and 400 ppm, respectively.

Example 11. Example 11 was carried out in an identical manner to Example 7, except that the interference platelets, satin red CP-211 and satin green CP-231, were added at concentrations of 800 ppm and 400 ppm, respectively.

Example 12. Example 12 was carried out in an identical manner to Example 7, except that the amount of Filler D was 3.50 g in total, and the interference platelets, satin red CP-211 and satin gold CP-201, were added at concentrations of 1000 ppm and 400 ppm, respectively.

Example 13. Example 13 was carried out in an identical manner to Example 12, except that the interference platelets, satin red CP-211 and satin green CP-231, were added at concentrations of 1000 ppm and 400 ppm, respectively.

Example 14. Example 14 was carried out in an identical manner to Example 12, the interference platelets, satin red CP-211 and satin green CP-231, were added at concentrations of 800 ppm and 600 ppm, respectively.

Comparison Example 4. Into a 100 cc container was carefully weighed 3.25 g of Filler E and 1.67 g of activated Dental Resin A. The contents were then mixed for 60 seconds using a Flactek Centrifugal speed-mixer operating at 2500 rpm, and this operation was repeated three times to ensure complete homogeneity.

Example 15. Example 15 was carried out in an identical manner to Comparison Example 4, except that the interference platelet, satin red CP-211, was added at concentration of 1000 ppm.

Example 16. Example 16 was carried out in an identical manner to Comparison Example 4, except that the interference platelet, satin red CP-211, was added at concentration of 2500 ppm.

Example 17. Example 17 was carried out in an identical manner to Comparison Example 4, except that the interference platelet, satin red CP-211, was added at concentration of 5000 ppm.

Example 18. Example 15 was carried out in an identical manner to Comparison Example 4, except that the interference platelets, satin red CP-211 and satin gold CP-201, were added at concentration of 1000 ppm, each.

General procedure to evaluate color match in Examples 1-18 and Comparison Examples 1-4. Examples 1-18 and comparison examples (1-4) were evaluated by measuring their color match to the dental shades A1-A4. Dental composite pastes were prepared for each example or comparison example using the procedure given above.

Preparation of Dental Shade Pads. The dental shades A1-A4 were procured from Kerr Dental. The procured paste was packed into a disk-shaped mold with dimension 6 cm diameter and 1 cm thickness. The paste was then cured by exposure to a 100 W blue light at a distance of 10 cm for 1 minute. After the disk cooled, the exposure was repeated. After 48 hours the hardened disk (pad) was removed from the mold and polished so that the surface of the pad was smooth and homogeneous in color. After approximately 48 hours, "cavities" measuring 4 mm wide and 3-4 mm deep were drilled into the face of each pad at distances of about 2 cm apart. The cavities were then filled with the Example and Comparison Example dental composites described above, or with Omnichroma®, such that the composite filled the "cavity" flush with the surface of the pad. The example pastes were then cured using a dental lamp by two consecutive exposures of 20 seconds each. After about 48 hours, color measurements were obtained from photographs using the procedure described above. This procedure was repeated for all shades A1, A2, A3 and A4.

The data obtained from Comparison Examples 1-3, Examples 1-14 and Omnichroma® are contained in Table 1.

TABLE 1

The color match of Examples 1-18 and Comparison examples C1-C4 for shades A1-A4, and the average color match.

| Example or Comparison Example | Filler* | Total filler Loading (wt. %) | Interference Platelet (IP) | Amount IP (ppm)** | Contrast Ratio | Color Match Shade A1 ΔE | Color Match Shade A2 ΔE | Color Match Shade A3 ΔE | Color Match Shade A4 ΔE | Average Color Match (all shades) ΔE |
|---|---|---|---|---|---|---|---|---|---|---|
| C1 | 85% Filler A/15% Filler B | 67 | none | 0 | 48.4 | 14.2 | | 11.5 | 3.6 | 9.8 |
| Ex. 1 | 85% Filler A/15% Filler B | 67 | Red | 800 | 60.7 | 6 | | 7.2 | 3 | 5.4 |
| Ex. 2 | 85% Filler A/15% Filler B | 67 | Gold | 500 | 61 | 8.8 | | 6 | 2.6 | 5.8 |
| Ex. 3 | D (1.510) | 67 | Red | 640 | 53.8 | 6.5 | 9 | 2.5 | 4.5 | 5.6 |
| Ex. 4 | C (1.518) | 67 | Red | 640 | 44.3 | 8.3 | | 9.3 | 7.3 | 8.3 |
| Ex. 5 | A (1.523) | 67 | Red | 640 | 42.8 | 6.5 | | 5.8 | 5.9 | 6.1 |
| C2 | A (1.523) | 70 | none | 0 | 30.5 | 10.8 | | 9.5 | 2.9 | 7.7 |
| Ex. 6 | A (1.523) | 70 | Red/Gold | 400/400 | 53.5 | 8.5 | | 7.7 | 10.1 | 8.8 |
| Ex. 7 | D (1.510) | 67 | Red | 1280 | 62 | 4.6 | 5.6 | 2.1 | 2.1 | 3.6 |
| Ex. 8 | C (1.518) | 67 | Red | 1280 | 55.7 | 4.8 | | 2.2 | 5.1 | 4.0 |
| Ex. 9 | A (1.523) | 67 | Red | 1280 | 51.9 | 6.2 | | 4.1 | 1.9 | 4.1 |
| C3 | D (1.510) | 67 | none | 0 | 43.6 | 12.9 | 10.2 | 8.8 | 5.4 | 9.3 |
| Ex. 10 | D (1.510) | 67 | Red/Gold | 800/400 | 63.6 | 8.1 | 2.2 | 5 | 9.9 | 6.3 |
| Ex. 11 | D (1.510) | 67 | Red/Green | 800/400 | 61.9 | 4.5 | 3 | 6.7 | 5.9 | 5.0 |
| Ex. 12 | D (1.510) | 70 | Red/Gold | 1000/400 | 64.3 | 8.6 | 2.5 | 4 | 6.6 | 5.4 |
| Ex. 13 | D (1.510) | 70 | Red/Green | 1000/400 | 71 | 5 | 2 | 5 | 9.1 | 5.3 |
| Ex. 14 | D (1.510) | 70 | Red/Green | 800/600 | 68.3 | 3.5 | 3.7 | 2.8 | 9.5 | 4.9 |
| C4 | E (1.535) | 65 | none | | 31.3 | 7.0 | 8.2 | 9.1 | 4.2 | 7.1 |
| Ex. 15 | E (1.535) | 65 | Red | 1000 | 63.4 | 4.9 | 4.2 | 4.6 | 3.2 | 4.2 |
| Ex. 16 | E (1.535) | 65 | Red | 2500 | 89.7 | 10.1 | 9.6 | 8.7 | 6.7 | 8.8 |
| Ex. 17 | E (1.535) | 65 | Red | 5000 | 91.8 | 14.2 | 10.1 | 8.9 | 7.3 | 10.1 |
| Ex. 18 | E (1.535) | 65 | Red/Gold | 1000/1000 | 73.2 | 8.3 | 4.9 | 5.7 | 8.4 | 6.8 |
| Omnichroma ® | | | | | 65.7 | 9.2 | 1.3 | 3.9 | 6.7 | 5.3 |

*The index of refraction of the filler is given in parentheses; in all cases the index of refraction of the polymer is 1.530
**The concentration of interference platelet is given in parts per million; for reference 0.1% = 1000 ppm Table 1 shows the color match of Examples 1-18 and Comparison examples C1-C4 for dental shades A1-A4, and the average color match. In all cases, the average color match is computed by averaging the ΔE values for all shades examined. The smaller the ΔE value the greater the color match to the dental shade. In general, it is believed that a color difference ΔE of less than 3.0 is indistinguishable to the average human observer. The comparison examples, which in all cases do not contain interference platelets, show average ΔE values of 9.8, 7.7, 9.3 and 7.1 for C1-C4, respectively. A human observer can easily distinguish the poor color match between these composites and the target dental shade, even from a relatively large distance. From Table 1, it is apparent that the color match potential of the composites is greatly improved by the addition of interference platelets, especially those having a reddish hue, and combinations of the red interference platelets with ether green or gold (yellow). The ability to match or adapt to a target color may be dependent upon the filler loading and also on the refractive index of the filler; each of which in turn influence the relative translucency of the cured dental composite. The degree of translucency is given by the contrast ratio. From Table 1, the best overall color adaptability is achieved when the contrast ratio is between about 55 and 75. Also from Table 1, interference platelets used at concentrations above about 2500 ppm show poor color adaptability and should be avoided.

Example 19. The dental composite of Example 11 was packed into the A1-A4 cylinder shades and cured and evaluated for color match as described below for each shade.

Example 20. Into a 100 cc container was carefully weighed 2.60 g of Filler E, 0.65 g of Filler F, 0.0040 g satin red, 0.0020 g satin green and 1.75 g of activated Dental Resin A. The interference platelets were pre-mixed in the resin to ensure homogeneity. The contents were then mixed for 60 seconds using a Flactek Centrifugal speed-mixer operating at 2500 rpm, and this operation was repeated three times to ensure complete homogeneity. The dental composite paste was stored at 25° C. in the dark when not being used. Cavities were filled with this dental composite, cured, and evaluated as described below.

Comparison Example 5. Prepared identical to Example 20, except the interference platelets were not added.

Example 21. Into a 100 cc container was carefully weighed 2.44 g of Filler D, 0.81 g of Filler F, 0.0040 g satin red, 0.0020 g satin green and 1.75 g of activated Dental Resin A. The interference platelets were pre-mixed in the resin to ensure homogeneity. The contents were then mixed for 60 seconds using a Flactek Centrifugal speed-mixer operating at 2500 rpm, and this operation was repeated three times to ensure complete homogeneity. The dental composite paste was stored at 25° C. in the dark when not being used. Cavities were filled with this dental composite, cured, and evaluated as described below.

Example 22. Into a 100 cc container was carefully weighed 2.80 g of Filler E, 0.70 g of Filler F, 0.0040 g satin red, 0.0020 g satin green and 1.75 g of activated Dental Resin A. The interference platelets were pre-mixed in the resin to ensure homogeneity. The contents were then mixed for 60 seconds using a Flactek Centrifugal speed-mixer operating at 2500 rpm, and this operation was repeated three times to ensure complete homogeneity. The dental composite paste was stored at 25° C. in the dark when not being used. Cavities were filled with this dental composite, cured, and evaluated as described below.

General procedure to evaluate color match in Examples 19-22 and Comparison Examples 5. Examples 19-22 and comparison example 5 were evaluated by measuring their color match to the dental shades A1-A4. Dental composite pastes were prepared for each example or comparison example using the procedure given above.

Cylinder Shades A1, A2, A3 and A4. SonicFil shades A1, A2, A3 and A4 were packed into cylindrical molds with dimensions 8 mm diameter and 1 cm length. The pastes were then cured by exposure to a 1000 mW dental lamp at a distance of 1 mm cm for 3×20 seconds. An additional exposure of 20 seconds was performed on the opposite side of the cylinder to ensure complete cure. After 48 hours the hardened cylinder was removed from the mold, and a "cavity" measuring 4 mm wide and 3-4 mm deep were drilled into the face of the cylinder. The cavity was then filled with an Example (19-22) or Comparison Example (C5), or with Omnichroma®, such that the composite filled the "cavity" flush with the surface of the cylinder. The paste was then cured using a dental lamp by two consecutive exposures of 20 seconds each. The cured paste and the face of the cylinder was then polished using ultra fine sandpaper. After about 48 hours, color measurements were obtained from photographs using the procedure described above. This procedure was repeated for all shades A1, A2, A3 and A4, and for all example and comparison examples. These cylinders, consisting of cured dental composites of various shades, were designed to mimic human teeth (of various shades) both in size, color, and aesthetics.

TABLE 2

The color match of Examples 19-22 and Comparison example C5 for shades A1-A4, and the average color match.

| Example or Control Example | Composite Composition | | | Optical Properties Contrast Ratio | Color Match Shade A1 Delta E | Color Match Shade A2 Delta E | Color Match Shade A3 Delta E | Color Match Shade A4 Delta E | Average Color Match |
|---|---|---|---|---|---|---|---|---|---|
| | Filler* | Total filler Loading (wt. %) | Interference Platelets | Amont IP** (ppm) | | | | | |
| Ex. 19 | D (1.510) | 65 | Red/green | 800/400 | 61.9 | 8.3 | 15.4 | 6.7 | 7.5 | 9.5 |
| Ex. 20 | E (1.535) and F(1.535) at a ratio of 80:20 | 65 | Red/green | 800/400 | 67.6 | 5.2 | 6.9 | 3.0 | 5.4 | 5.1 |
| C5 | E (1.535) and F(1.535) at a ratio of 80:20 | 65 | none | 0 | 41.8 | 15.0 | 14.7 | 6.5 | 1.5 | 9.4 |
| Ex. 21 | D (1.510) and F(1.535) at a ratio of 75:25 | 65 | Red/green | 800/400 | 66.3 | 5.8 | 7.6 | 3 | 4.3 | 5.2 |
| Ex. 22 | E (1.535) and F(1.535) at a ratio of 80:20 | 70 | Red/green | 800/400 | 68 | 3.5 | 2.6 | 1.4 | 3.2 | 2.7 |
| Omnichroma | | | | | 65.7 | 7.4 | 8 | 4.5 | 1.7 | 5.4 |

*The index of refraction of the filler is given in parentheses; in all cases the index of refraction of the polymer is 1.530
**The concentration of interference platelet is given in parts per million; for reference 0.1% = 1000 ppm Table 2 shows the color match of Examples 19-22 and Comparison example C5 for shades A1-A4, and the average color match. The data show that upon inclusion of red and green interference reflectors, color match is significantly improved, especially for the whiter shades A1 and A2. Further, when used in combination with fillers that have a refractive index near that of the polymer refractive index, and fillers which have a significant component of primary particle size greater than 30 nm, the color adaptability is nearly indistinguishable for all shades A1-A4, as in Example 22.

I claim:

1. A curable dental composition comprising a photocurable resin, at least one filler, a photoinitiator and at least one interference platelet to form a translucent composite in a colored cavity surrounding said composite, wherein said translucent composite mimics the color of said surrounding cavity, wherein the at least one filler and the photocurable resin both have refractive indices and the difference between the refractive index of the filler and the refractive index of the photocurable resin after curing is not greater than 0.03.

2. The curable dental composition of claim 1, wherein said curable dental composition is a disk having a thickness of 1 mm and a contrast ratio of between 40 and 85.

3. The curable dental composition of claim 1, wherein said curable dental composition is a disk having a thickness of 1 mm and a contrast ratio of between 55 and 75.

4. The curable dental composition of claim 1, wherein the at least one interference platelet is reflective or scattering in the visible region of a spectrum.

5. The curable dental composition of claim 1, wherein the at least one interference platelet is reflective or scattering in the red and green region of a spectrum.

6. The curable dental composition of claim 1, wherein the at least one interference platelet is reflective or scattering in the red and yellow region of a spectrum.

7. The curable dental composition of claim 1, wherein the at least one interference platelet has a mean particle diameter between 5 and 100 microns.

8. The curable dental composition of claim 1, wherein the at least one interference platelet has a mean particle diameter between 5 and 50 microns.

9. The curable dental composition of claim 1 wherein the filler has a refractive index that is less than the refractive index of the photocurable resin after curing.

10. The curable dental composition of claim 1, wherein the at least one interference platelet comprises less than 2500 parts per million of said curable dental composition.

11. The curable dental composition of claim 1, wherein the at least one interference platelet comprises between 100 and 1500 part per million of said curable dental composition.

12. The curable dental composition of claim 11 wherein the said filler comprises at least 50% silica, and wherein at least a portion of the silica has a primary particles size greater than 30 nm.

13. The curable dental composition of claim 1, wherein the at least one interference platelet(s) is/are chosen such that they match dental A shades from a classical shade guide.

14. The curable dental composition of claim 1, wherein the at least one interference platelet(s) is/are chosen such that they match dental C shades from a classical shade guide.

15. The curable dental composition of claim 1, wherein the at least one interference platelet(s) is/are chosen such that they match dental D shades from a classical shade.

16. The curable dental composition of claim 1, wherein said at least one interference platelet is a microparticle whose thickness is selected such that it reflects or scatters specific colors or wavelengths of light.

17. The curable dental composition of claim 1, wherein said at least one interference platelet is a layer like structure of two or more materials.

18. The curable dental composition of claim 1, wherein said at least one interference platelet has a diameter of 5-100 microns, a thicknesses of less than one micron and is chosen to form an interference pattern with actinic radiation.

19. A curable dental composition comprising a photocurable resin, at least one filler, a photoinitiator and at least one interference platelet to form a translucent composite in a colored cavity surrounding said composite, wherein said translucent composite mimics the color of said surrounding cavity, wherein the at least one interference platelet comprises between 100 and 1500 part per million of said curable dental composition, wherein the said filler comprises at least 50% silica, and wherein at least a portion of the silica has a primary particles size greater than 30 nm.

20. The curable dental composition of claim 1, wherein said curable dental composition is a disk having a thickness of 1 mm and a contrast ratio of between 40 and 85.

* * * * *